(12) United States Patent
Hara et al.

(10) Patent No.: US 7,892,334 B2
(45) Date of Patent: Feb. 22, 2011

(54) PACKAGE OF VOLATILE SUBSTANCE AND AIR CONDITIONER FOR VEHICLES PROVIDED WITH THE PACKAGE

(75) Inventors: Shinichi Hara, Saitama (JP); Akihiko Yoshida, Saitama (JP); Frederic Giraud, Le Perray en Yvelines (FR); Frederic Ladrech, Maurepas (FR); Yoshie Aoki, Saitama (JP); Masumi Yamaguchi, Tokyo (JP); Kiyoshi Kamei, Fukui (JP); Hidenao Saito, Fukui (JP)

(73) Assignees: Valeo Thermal Systems Japan Corporation, Kumagaya-shi (JP); Valeo Systemes Thermiques, Le Mesnil Saint Denis (FR); Rengo Co., Ltd., Osaka-shi (JP)

( * ) Notice: Subject to any disclaimer, the term of this patent is extended or adjusted under 35 U.S.C. 154(b) by 686 days.

(21) Appl. No.: 11/911,439

(22) PCT Filed: Apr. 12, 2005

(86) PCT No.: PCT/JP2005/007105

§ 371 (c)(1),
(2), (4) Date: Oct. 12, 2007

(87) PCT Pub. No.: WO2006/112005

PCT Pub. Date: Oct. 26, 2006

(65) Prior Publication Data

US 2008/0210094 A1   Sep. 4, 2008

(51) Int. Cl.
*B01D 46/00* (2006.01)
*B65D 85/00* (2006.01)

(52) U.S. Cl. .................. 96/222; 261/104; 261/DIG. 88

(58) Field of Classification Search ..................... 95/43; 96/4, 7, 11, 12, 13, 14, 222; 215/261; 239/60; 261/104, DIG. 88
See application file for complete search history.

(56) References Cited

U.S. PATENT DOCUMENTS 4,094,119 A * 6/1978 Sullivan ....................... 53/400

(Continued)

FOREIGN PATENT DOCUMENTS

JP          2 88655       7/1990

(Continued)

*Primary Examiner*—Duane Smith
*Assistant Examiner*—Sonji Turner
(74) *Attorney, Agent, or Firm*—Oblon, Spivak, McClelland, Maier & Neustadt, L.L.P.

(57) ABSTRACT

The object of the present invention is to provide a package of a volatile substance, which comprises a bag having a volatile substance with an antibacterial action enclosed therein, and a case having the bag enclosed therein, wherein the case is allowed to have a size and shape complying with the amount of a volatile substance having permeated the bag so that the shape of the case can be adapted to the volumes and shapes of various air conditioners, while the volatile substance can be volatilized at a predetermined rate. The package of a volatile substance according to the invention comprises a source generating the volatile substance, and a case which has the volatile-substance source enclosed therein and which has a wall at least a part of which is made of a gas-permeable resin, wherein the case is characterized in that a value expressed by the formula X×Z/Y is 200000 to 1500000 wherein X represents the surface area (mm$^2$) of the wall; Y represents the thickness (mm) of the wall; and Z represents the vaporization amount (mg/day) of the volatile substance volatilized by the volatile-substance source per day in an atmosphere at 30° C.

17 Claims, 11 Drawing Sheets

U.S. PATENT DOCUMENTS

| | | | |
|---|---|---|---|
| 4,356,969 A * | 11/1982 | Obermayer et al. | 239/6 |
| 4,605,165 A * | 8/1986 | Van Loveren et al. | 239/6 |
| 4,614,299 A * | 9/1986 | Van Loveren et al. | 239/6 |
| 5,439,100 A * | 8/1995 | Gordon et al. | 206/5 |
| 6,524,375 B2 * | 2/2003 | Brun | 96/222 |
| 2001/0039882 A1 * | 11/2001 | Brun | 96/222 |

FOREIGN PATENT DOCUMENTS

| | | |
|---|---|---|
| JP | 63-075430 | 4/1998 |
| JP | 11 211126 | 8/1999 |
| JP | 2000 88270 | 3/2000 |
| JP | 2000 318775 | 11/2000 |
| JP | 2001 122711 | 5/2001 |
| JP | 2001 149459 | 6/2001 |
| JP | 2004 224382 | 8/2004 |

* cited by examiner

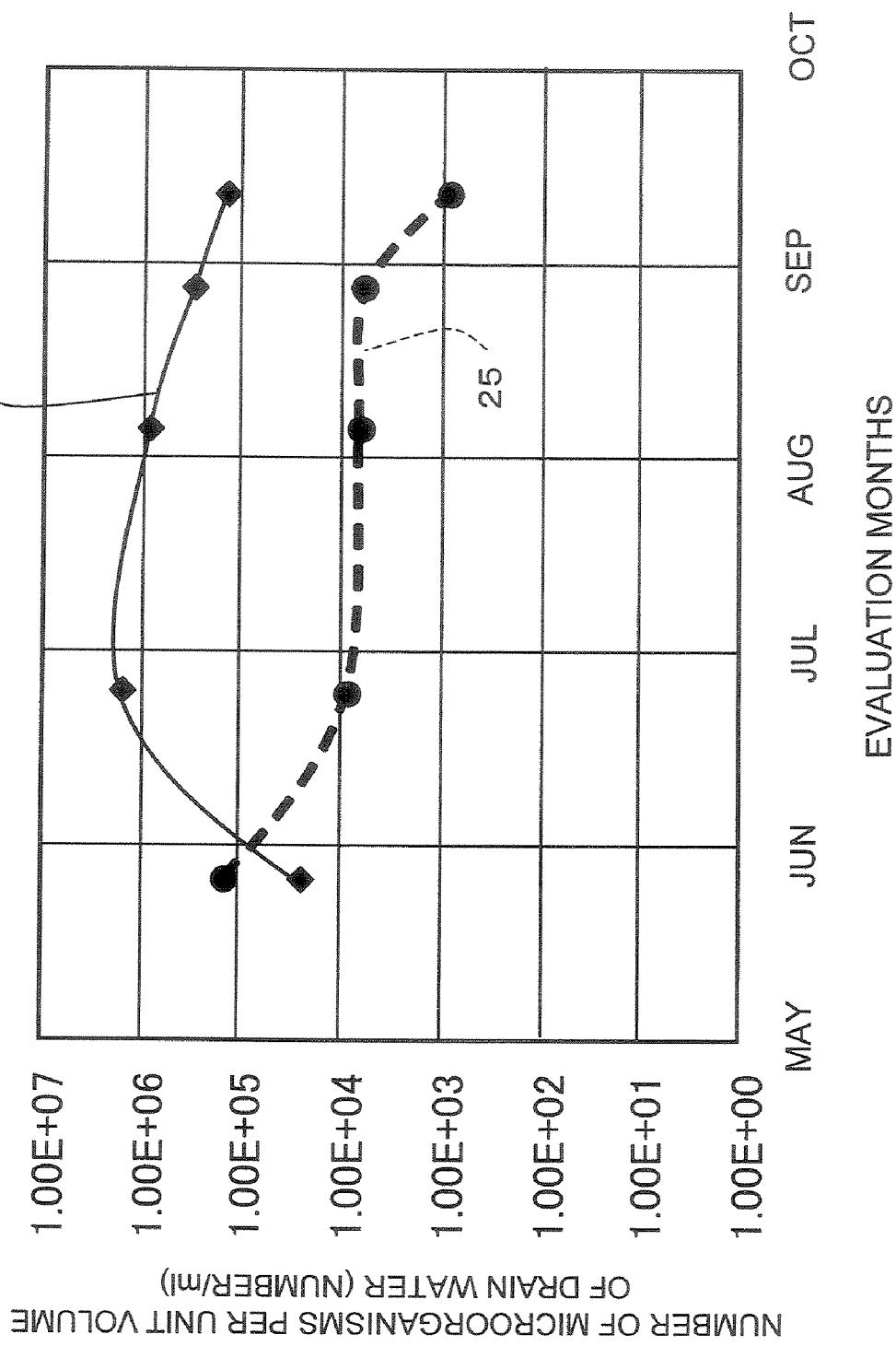

PACKAGE OF VOLATILE SUBSTANCE AND AIR CONDITIONER FOR VEHICLES PROVIDED WITH THE PACKAGE

TECHNICAL FIELD

The present invention relates to a package which a volatile substance permeates and an air conditioner for vehicles provided with the package.

BACKGROUND ART

Conventionally, blowout of an offensive odor upon actuation of an air conditioner for vehicles has been problematic. As the reason for this offensive odor, mention can be made of the activity of microorganisms such as bacteria proliferated inside air conditioners. The inside of an air conditioner is an environment which favors bacterial proliferation because of dew condensation water adhering to an evaporator during operation of the air conditioner. By the action of a large amount of proliferated bacteria, the inside of an air conditioner is filled with an offensive odor. Antibacterial treatment and drying treatment in the inside of an air conditioner have been considered as countermeasures against this offensive odor.

There is a method of compounding an antibacterial agent into a resin inside an air conditioner as one of antibacterial treatments. In this method, however, the effect of an antibacterial agent is lost when dust accumulates on the antibacterial agent. As a countermeasure, use of a volatile antibacterial agent has been proposed (see, for example, Patent Documents 1 to 3). In the prior art inventions, a volatile antibacterial agent is placed inside the air conditioner. It is however difficult to apply the prior art inventions to an air conditioner for a motor vehicle. The temperature in a motor vehicle becomes very high in summer, and the temperature in an air conditioner can sometimes reach about 50° C. When the temperature is raised as just described, the amount of the antibacterial agent volatilized is increased, and thus the antibacterial agent is consumed in a short period of time.

To solve this problem, an invention directed to a case housing an antibacterial agent has been made (see, for example, Patent Document 4). In the Patent Document 4, attention is focused on that when a case using allyl isothiocyanate (AIT) as an antibacterial agent is made of polypropylene, a part of volatilized AIT passes through the polypropylene. By utilizing this characteristic, the volatilization rate of the volatile substance permeating through the case is controlled by housing the volatile substance in a gas-permeable bag and changing the thickness of the case and the surface area of the case.

Patent Document 1
   Japanese Patent Laid-Open No. Hei 11-211126

Patent Document 2
   Japanese Patent Laid-Open No. 2000-88270

Patent Document 3
   Japanese Patent Koukoku No. Hei 6-78821

Patent Document 4
   Japanese Patent Laid-Open No. 2004-224382

SUMMARY OF THE INVENTION

Problem to be Solve by the Invention

When the above-described case housing an antibacterial agent is to be arranged in the inside of an air conditioner for vehicles, the case should have a shape suitable for the shape of a ventilation duct of an air conditioner in which the ventilation duct has a shape varying depending on the type of vehicle. With advances in vehicles for diversification and higher performance, a volume and shape which can be possessed by an air conditioner are endowed with various conditions. Accordingly, various sizes and shapes of a case housing an antibacterial agent can be selected for arranging the case in an air conditioner, and the case is required to be capable of volatilizing an antibacterial component at a predetermined rate. In the Patent Document 4, the volatilization amount of a volatile substance volatilized per day by a bag as a source generating the volatile substance (hereinafter, the volatilization amount of a volatile substance per day is referred to as "volatilization amount") is not taken into consideration, and it is thus not always possible to select a case having a size and shape suitable for the volatilization amount from a bag undergoing a change resulting from external factors such as ambient temperature. In addition, the antibacterial component cannot be provided at a suitable rate.

Accordingly, the object of the present invention is to provide a package of a volatile substance, which comprises a source generating a volatile substance having an antibacterial action, and a package of a volatile substance which is a case having the volatile-substance source enclosed therein, wherein the case is allowed to have a size and shape complying with the volatilization amount of a volatile substance volatilized by the source so that the shape of the case can be adapted to the volumes and shapes of various air conditioners, while the volatile substance can be volatilized at a predetermined rate.

Means for Solving Problem

To solve the problem, the package of a volatile substance according to the present invention comprises a source generating the volatile substance, and a case which has the volatile-substance source enclosed therein and which has a wall at least apart of which is made of a gas-permeable resin, wherein the case is characterized in that a value expressed by the formula X×Z/Y is 200000 to 1500000 wherein X represents the surface area ($mm^2$) of the wall made of the resin; Y represents the thickness (mm) of the wall made of the resin; and Z represents the vaporization amount (mg/day) of the volatile substance volatilized by the volatile-substance source per day in an atmosphere at 30° C.

In one embodiment of the package of a volatile substance according to the present invention, the volatile-substance source is preferably a gas-permeable bag having the volatile substance enclosed therein.

In another embodiment of the package of a volatile substance according to the present invention, the volatile substance is preferably formed into a mixture having the volatile substance supported in an arbitrary compounding ratio on at least one or more kind of support, and the mixture is enclosed in the bag. By suitably establishing the type of the support and the compounding ratio, the package of a volatile substance can allow a desired amount of the volatile substance to permeate therethrough.

In another embodiment of the package of a volatile substance according to the present invention, the volatile-substance source is a mixture having the volatile substance supported in an arbitrary compounding ratio on at least one or more kind of support. Even if the source generating a volatile substance is the above-mentioned mixture and is enclosed directly in the case, the package of a volatile substance can allow a predetermined amount of the volatile substance to permeate therethrough.

In another embodiment of the package of a volatile substance according to the present invention, the case preferably allows the volatile substance to permeate therethrough at a rate of 5 to 30 mg/day in an atmosphere at 30° C. This rate brings about an amount effective in suppressing microbial growth in a vehicle air conditioner and can allow this amount of the volatile substance to be volatilized from the package.

In another embodiment of the package of a volatile substance according to the present invention, the bag is a bag provided partially or wholly with a permeation-regulating layer for regulating the permeation amount of the volatile substance. By suitably establishing the type and thickness of the permeation-regulating layer, the package of a volatile substance can allow a predetermined amount of the volatile substance to permeate therethrough.

In another embodiment of the package of a volatile substance according to the present invention, the bag allows the volatile substance to permeate therethrough at a rate of 10 to 1000 mg/day in an atmosphere at 30° C. This rate is preferable rate in order that the amount of the volatile substance permeated from the case is 5 to 30 mg/day in an atmosphere at 30° C.

In another embodiment of the package of a volatile substance according to the present invention, the package encompasses a case when the volatile substance is an isothiocyanate compound. The isothiocyanate compound can be used as an antibacterial agent and is a highly safe substance which can also be utilized in foods, and this compound can be volatilized from the package.

In another embodiment of the package of a volatile substance according to the present invention, the package encompasses a case when the resin forming the case is polypropylene. By forming the case wall from polypropylene, the volatile substance can permeate through the wall. In addition, polypropylene is excellent in chemical resistance and can thus prevent deterioration with the volatile substance.

The vehicle air conditioning device according to the present invention comprises the above-mentioned package of a volatile substance arranged in a ventilation duct.

EFFECT OF THE INVENTION

In the package of a volatile substance comprising a source generating the volatile substance and a case having the volatile-substance source enclosed therein according to the present invention, the case is allowed to have a size and shape complying with the volatilization amount of the volatile substance volatilized by the source, whereby the shape of the case can be adapted to the volumes and shapes of various air conditioners, while the volatile substance can be volatilized at a predetermined rate.

BRIEF DESCRIPTION OF DRAWINGS

FIG. 11 is a graph showing a difference in antibacterial effect between HVAC provided with the package of a volatile substance and HVA not provided with the package of a volatile substance.

EXPRESSION OF REFERENCE NUMERALS

Numbers have the following means:

1 is a case; 2, a housing part; 3, an upper lid; 4, a bag; 5, a mixture; 6, a wall; 7, a nonwoven fabric sheet; 8, a polyethylene sheet; 9, a biaxially stretched polypropylene sheet; 10, a polyethylene sheet; 11, a volatile substance; 12, a space between a bag and a mixture; 13, a space between a case and a bag; 17 to 26, lines in graphs; 50, an instrument panel; 51, an internal space in an instrument panel; 52, a fresh-air inlet; 53, an in-car air suction opening; 54, a blower unit; 55, an evaporator; 56, an in-car blowout opening; 57, an inside/outside air switching box; 58, a heater core; 59, a housing; 60a, 60b, 60c, ventilation ducts; 61, an intake door; 62, a filter unit; 100, a package; 200, HVAC; and 300, a package.

BEST MODE FOR CARRYING OUT THE INVENTION

Hereinafter, the present invention is described by reference to the drawings. The present invention is not limited to the following embodiments.

First Embodiment

The package of a volatile substance according to the present invention comprises a source generating the volatile substance, and a case which has the volatile-substance source enclosed therein and which has a wall at least a part of which is made of a gas-permeable resin, wherein the case is characterized in that a value expressed by the formula X×Z/Y is 200000 to 1500000 wherein X represents the surface area ($mm^2$) of the wall made of the resin; Y represents the thickness (mm) of the wall made of the resin; and Z represents the vaporization amount (mg/day) of the volatile substance volatilized by the volatile-substance source per day in an atmosphere at 30° C.

The package of a volatile substance according to this embodiment, the volatile-substance source may be a gas-permeable bag having the volatile substance enclosed therein or may be a gas-permeable bag in which a mixture having the volatile substance supported in an arbitrary compounding ratio on at least one or more kind of support is enclosed.

Preferably, the case allows the volatile substance to permeate therethrough at a rate of 5 to 30 mg/day in an atmosphere at 30° C. This rate bring about an amount effective in suppressing microbial growth in a vehicle air conditioner, and when the rate is less than 5 mg/day, sufficient antimicrobial performance cannot be achieved, while when the rate is greater than 30 mg/day in an atmosphere at 30° C., the volatile substance upon an increase in temperature in an air conditioner permeates the case more than necessary, thus extremely reducing the lifetime of the package.

Figure 1:
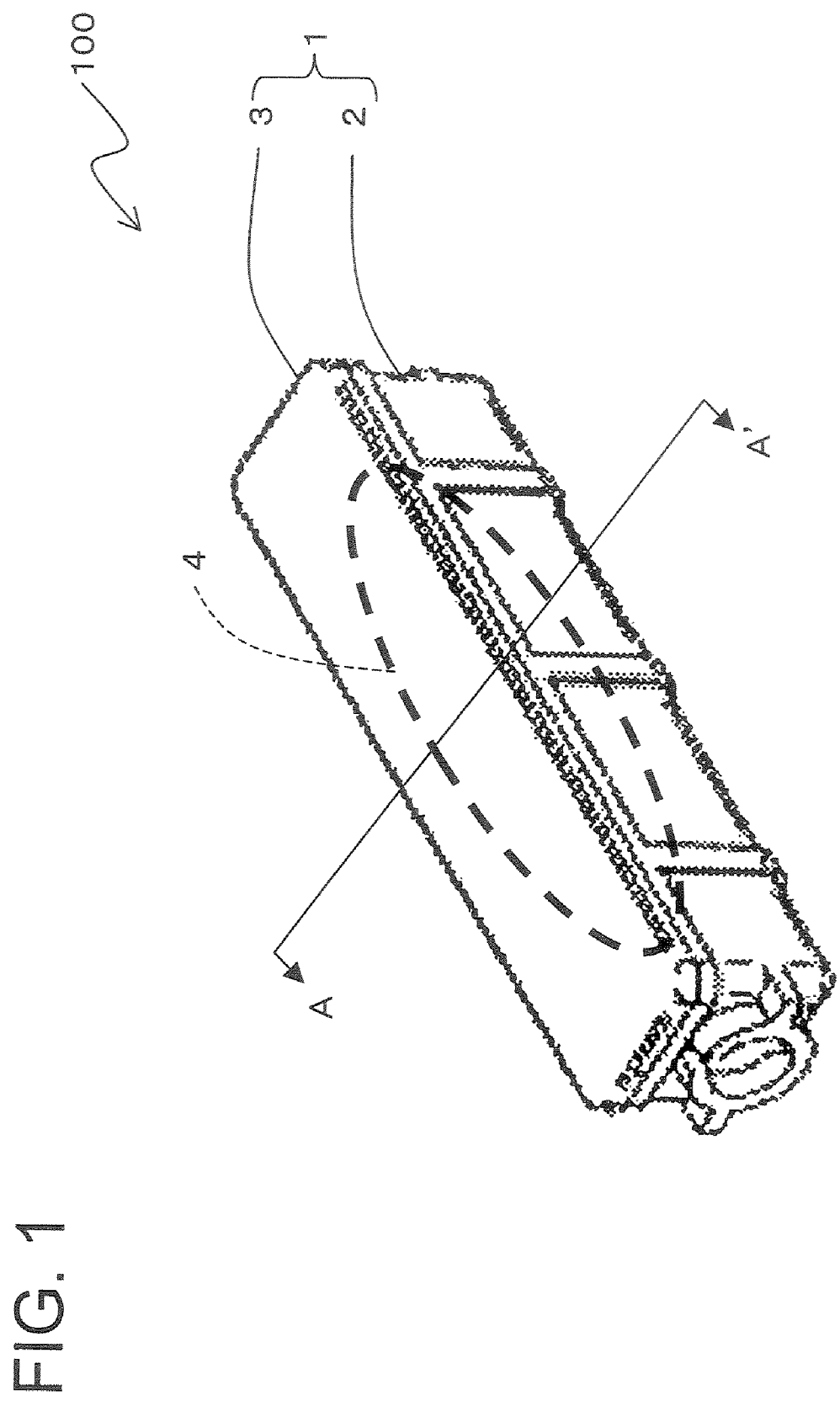
FIG. 1 is a perspective view of the package of a volatile substance in accordance with the first embodiment.
Figure 2:
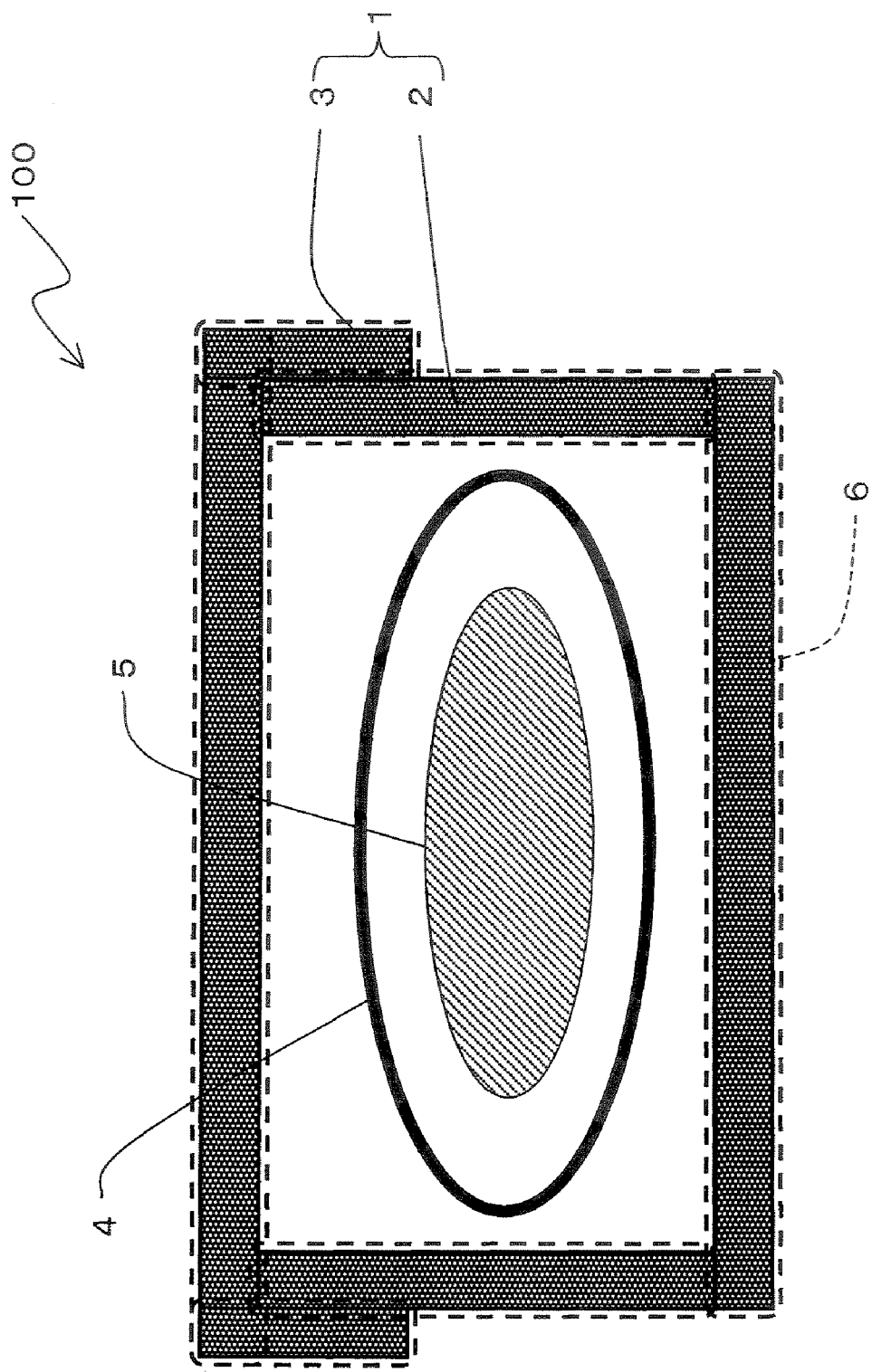
FIG. 2 is a schematic view of a section A-A' of the package of a volatile substance in accordance with the first embodiment.

The package of a volatile substance in accordance with this embodiment is described by reference to FIGS. 1 and 2. FIG. 1 is a perspective view of the package 100 in accordance with this embodiment. FIG. 2 is a schematic view of a section A-A' of the package 100 shown in FIG. 1.

The package 100 comprises a mixture 5 having a volatile substance supported on a support, a bag 4, and a case 1. The mixture 5 is enclosed in the bag 4, and the bag 4 is enclosed in the case 1. The case 1 is composed of a housing part 2 and an upper lid 3. The bag 4 has gas permeability. At least a part of wall 6 of the case 1 has gas permeability.

The volatile substance is preferably an isocyanate compound. Allyl isothiocyanate (AIT) is particularly preferable among the isothiocyanate compound. AIT is a compound known as a major component of Japanese horseradish, can be used as an antibacterial agent, and is a highly safe substance which can also be utilized in foods. When AIT is used, AIT can permeate through wall 6 of the case 1 if polypropylene is used as the material of the wall 6. When the source generating a volatile substance is to be formed into a bag 4 having the volatile substance enclosed therein, the volatile substance may be enclosed directly in bag 4 or may be enclosed as a mixture 5 having the volatile substance supported in an arbitrary compounding ratio on at least one or more kind of support. The compounding ratio refers to the mass content of the volatile substance in the mixture 5. The mixture 5 having the volatile substance supported therein can be exemplified by the mixture in arbitrary forms such as liquid, semiliquid having liquid kneaded in a resin, and powder, granules or solid having liquid supported on another solid. A support for supporting the volatile substance include, for example, resins such as rosin, rosin ester and paraffin wax, and solids such as pulp, paper, cellulose particles (particularly porous cellulose particles, foamed cellulose beads), zeolite, alumina, silica gel and calcium silicate. Nonvolatile oil, a light stabilizer and an antioxidant may also be incorporated into the mixture 5.

The bag 4 is made of a gas-permeable material. The material of the bag 4 is not particularly limited. The material varies depending on the type of the volatile substance and may be for example plastics such as polyethylene, non-stretched polypropylene, biaxially stretched polypropylene and polyethylene terephthalate, a nonwoven fabric, and a paper. These materials are used to prepare sheets, and a single sheet may be used to form bag 4.

Preferably, the bag 4 is formed by enclosing the mixture 5 having the volatile substance supported in an arbitrary compounding ratio on at least one or more kind of support and simultaneously having a permeation-regulating layer for regulating the permeation amount of the volatile substance formed in a part or the whole of the bag 4. The permeation-regulating layer is for example a laminate of the above-mentioned sheets different in their material to attain a desired permeation amount by utilizing a difference in the permeation amount of the volatile substance through the respective sheets. The material of the permeation-regulating material is not particularly limited. The material may be for example plastics such as polyethylene, non-stretched polypropylene, biaxially stretched polypropylene and polyethylene terephthalate, or a nonwoven fabric or a paper. These materials may be used to prepare sheets, and a laminate of a plurality of such sheets may be formed to provide bag 4 with a permeation-regulating layer. By suitably establishing the type and compounding ratio of the support or the type and thickness of the permeation-regulating layer, the resulting package of a volatile substance can allow a desired amount of the volatile substance to permeate therethrough. By enclosing the volatile substance in a compounding ratio of 10 to 90%, preferably 20 to 70%, in the above-mentioned bag 4, the case 1 can allow permeation of the volatile substance in an amount effective in suppressing microbial growth in an air conditioner for vehicles.

Figure 3:
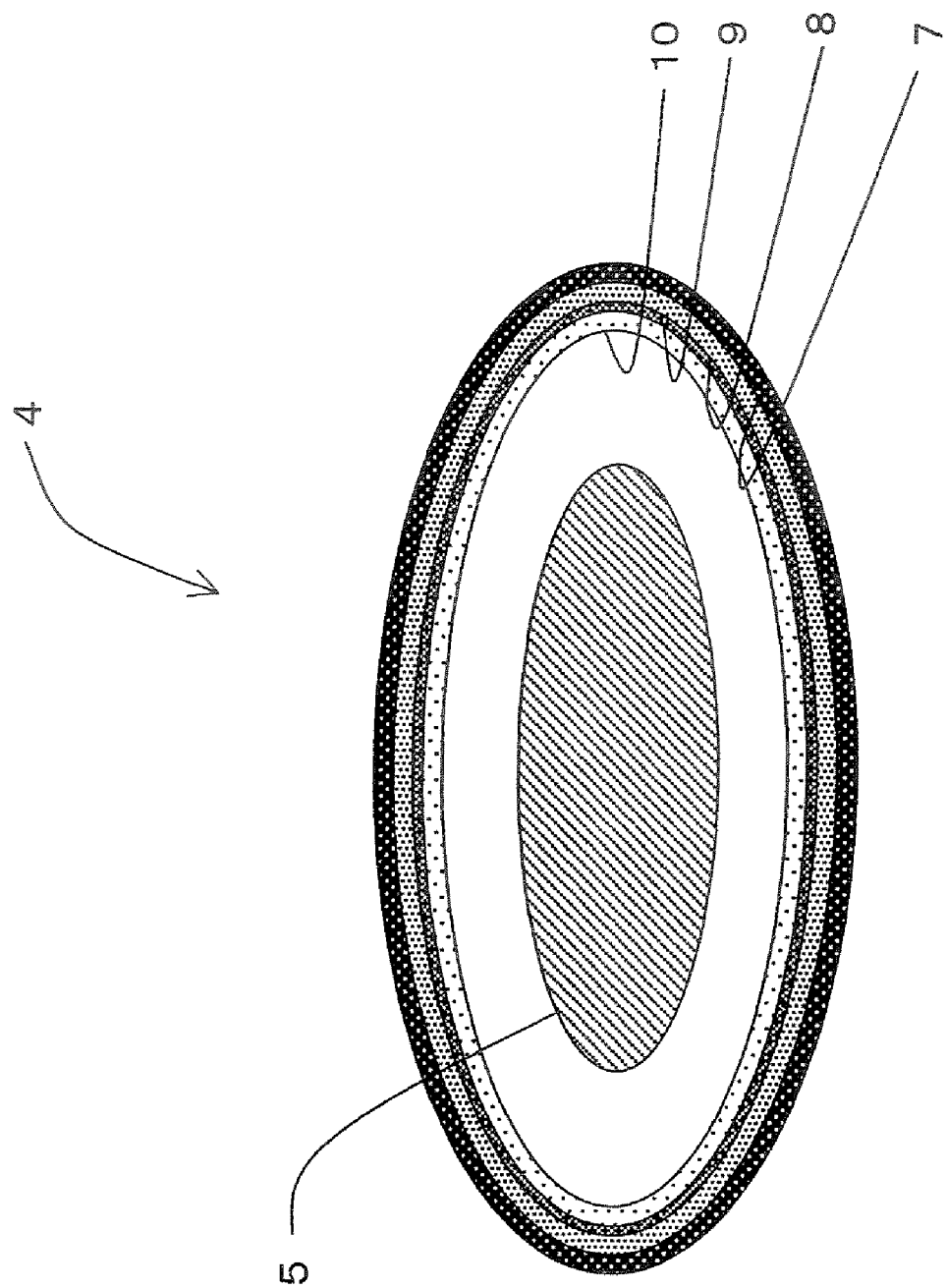
FIG. 3 is an illustration showing an example of a laminate of the bag in the first embodiment.

One example of bag 4 having a permeation-regulating layer formed therein is shown in FIG. 3. The bag 4 comprises a sheet 7 consisting of a nonwoven fabric, a sheet 8 consisting of polyethylene, a sheet 9 consisting of biaxially stretched polypropylene and a sheet 10 consisting of polyethylene laminated in this order from the outside. By forming the permeation-regulating layer in this manner, the amount of the volatile substance permeating the bag 4 can be suitably established. In the bag 4 in FIG. 3, the sheet 7 consisting of a nonwoven fabric is a sheet for preventing the surface of the bag from being damaged upon contacting with the outside. The inside sheet 10 consisting of polyethylene serves as an adhesive layer for enclosing the mixture 5.

Such bag 4 volatilizes the volatile substance, preferably at a rate of 10 to 1000 mg/day in an atmosphere at 30° C. This is because at a rate of less than 10 mg/day, the volatilization amount from the case 1 is too low to attain sufficient antimicrobial performance, while at a rate of higher than 1000 mg/day, the volatile substance upon an increase in temperature in an air conditioner is volatilized more than necessary, thus extremely reducing the lifetime of the package 100. For maintaining this volatilization amount, the thickness of the bag 4 for example is preferably 40 to 180 μm, more preferably 70 to 140 μm. By regulating the thickness of the bag in the range described above, the volatilization amount of the volatile substance volatilized by the bag can be a suitable amount, and the volatile substance in an amount effective in suppressing microbial growth in an air conditioner can be volatilized from the package. The bag 4 can be formed for example by laminating the above-mentioned sheets wherein the sheet 7 consisting of a nonwoven fabric is 50 μm, the sheet 8 consisting of polyethylene is 15 μm, the sheet 9 consisting of biaxially stretched polypropylene is 40 μm, and the sheet 10 consisting of polyethylene is 30 μm so that the thickness of the bag 4 as a whole becomes 135 μm.

External and internal spaces of the case 1 are divided from each other by wall 6. FIG. 2 shows an example of the case 1, the whole of which is formed from a wall made of a gas-permeable resin. As shown in FIG. 2, both a wall of housing part 2 and a wall of upper lid 3 may be made of a gas-permeable resin; alternatively, only one of the wall of housing part 2 and the wall of upper lid 3 may be made of a gas-permeable resin. By suitably selecting the part of wall 6 made of the resin, the surface area of the gas-permeable resin wall can be regulated. The gas-permeable resin is particularly preferably polypropylene. Polypropylene is a suitable material for allowing AIT to permeate therethrough. The wall 6 may be a transparent or semitransparent wall using polypropylene as the wall material, or may be made clouded by mixing talc in polypropylene. Alternatively, polypropylene may be colored in arbitrary color by adding a pigment.

The number of bags 4 enclosed in the case 1 is not particularly limited. An intended volatilization amount of the volatile substance may be achieved by using one bag 4, or an intended volatilization amount of the volatile substance may be achieved by the total amount of the volatile substance volatilized from a plurality of bags 4. A combination of bags 4 containing different volatile substances may also be used.

The bag 4 may be fixed with a support medium (not shown) in the case 1 or may not be supported.

Figure 4:
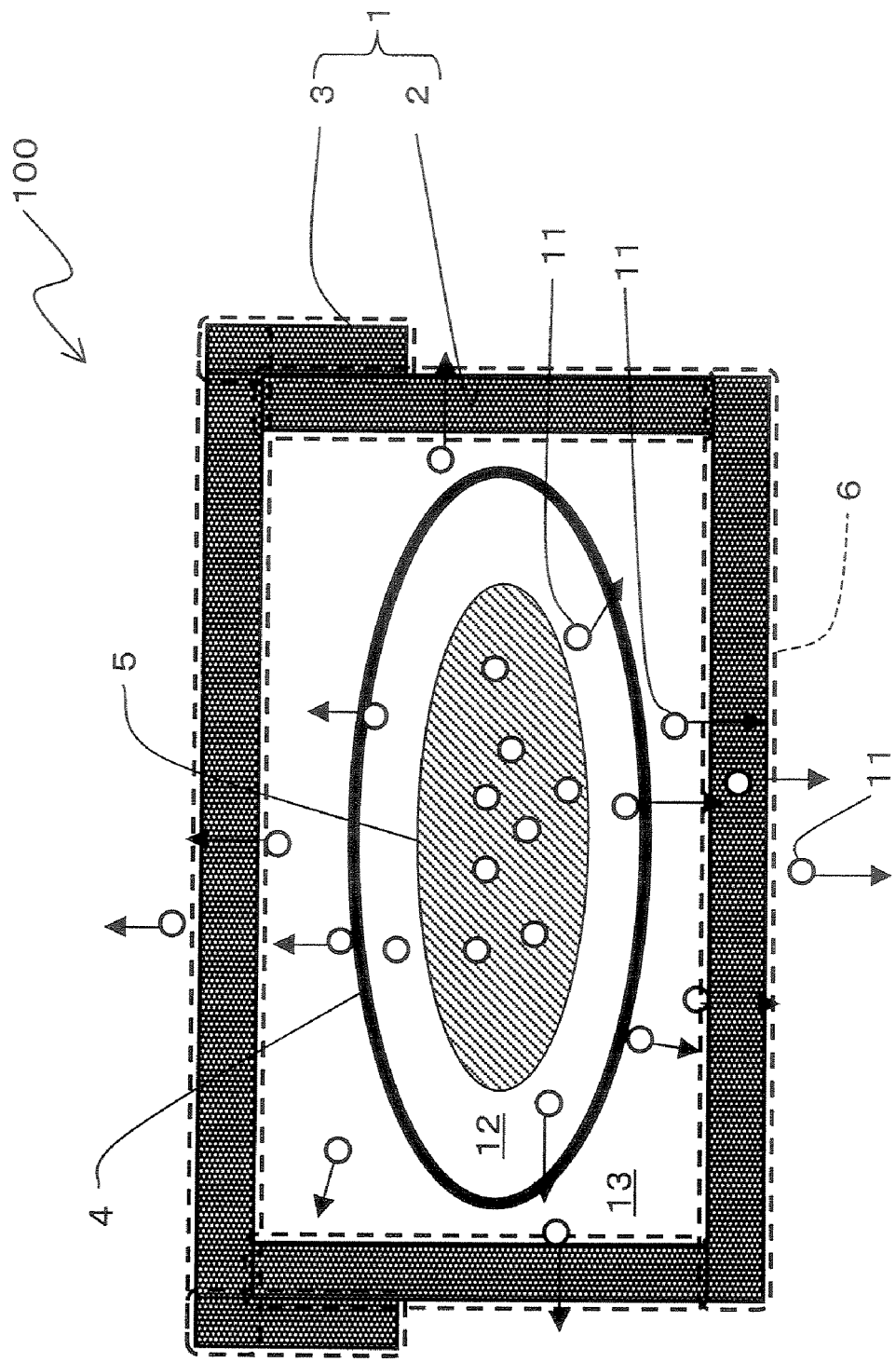
FIG. 4 is an illustration showing the state of permeation of the volatile substance.

Then, the state of permeation of the volatile substance is shown in FIG. 4. First, a space 12 between the bag 4 and mixture 5 is filled with the volatile substance 11 vaporized from the mixture 5 containing the volatile substance. Due to a difference in concentration of the volatile substance 11 between the space 12 and a space 13 between the case 1 and bag 4, the vaporized volatile substance 11 permeates the bag 4 and is then released from the bag 4 to the space 13. When the space 13 is filled with the volatile substance 11 having permeated the bag 4, the volatile substance 11 having permeated the bag 4 will, due to a difference in concentration of the volatile substance 11 between the space 13 and an external space of the package 100, permeate a wall 6 followed by being released from the wall 6 to the external space. In this manner, the volatile substance 11 is volatilized from the package 100.

Figure 5:
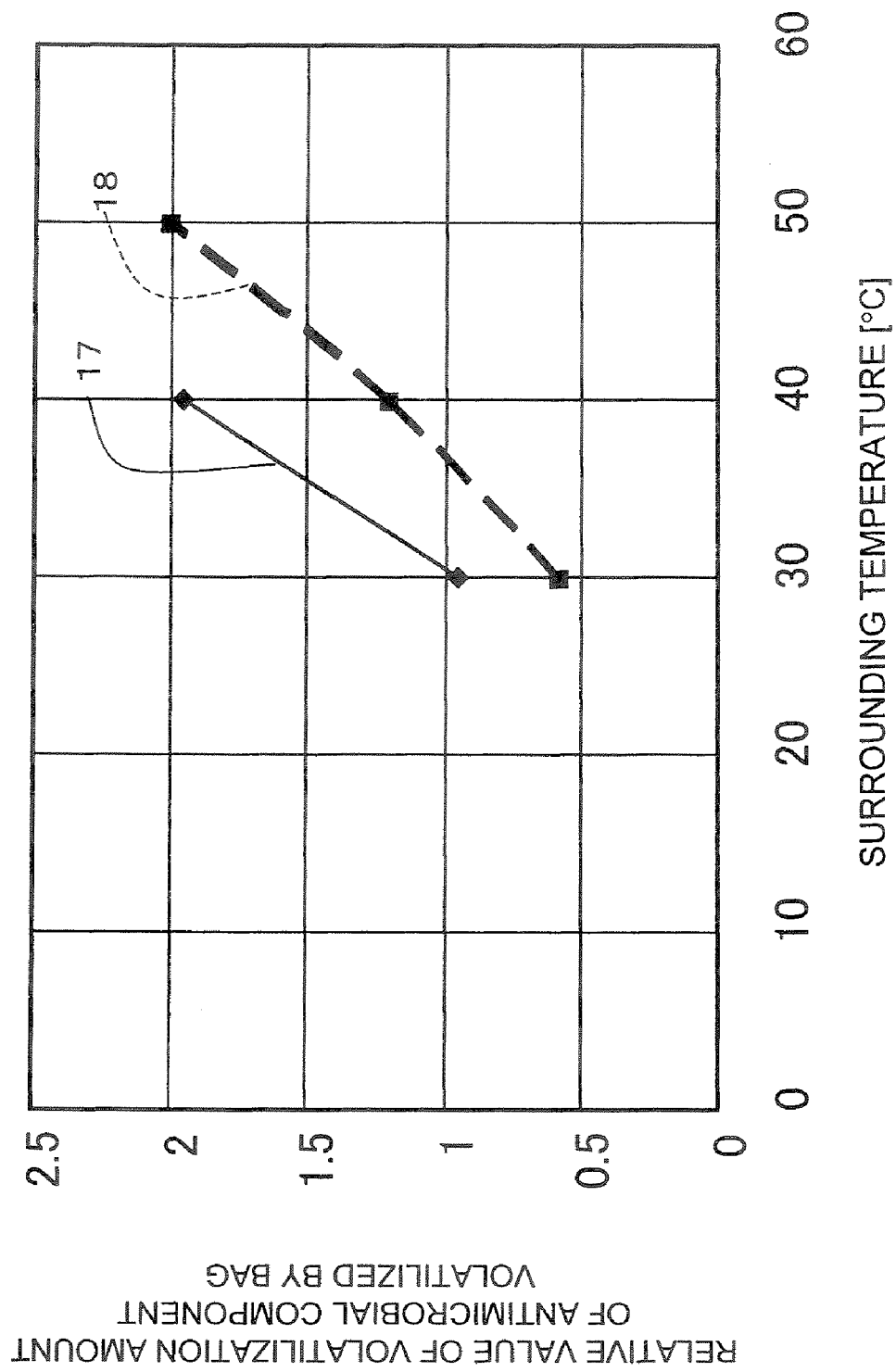
FIG. 5 is a graph showing the relationship between the compounding ratio of the antibacterial component and the amount of the antibacterial component volatilized by the bag.

FIG. 5 is a graph showing the relationship between the compounding ratio of the antibacterial component in a mixture containing the antibacterial component as a volatile substance and the volatilization amount of the antibacterial component volatilized by the bag. In FIG. 5, the surrounding temperature (° C.) is shown on the abscissa, and the relative amount of the antibacterial component volatilized by the bag is shown on the ordinate. The compounding ratio of the antibacterial component was used at 2 levels (levels 1 and 2). The compounding ratio at level 2 is twice as high as the compounding ratio at level 1. Specifically, level 1 was a compounding ratio of 30%, while level 2 was a compounding ratio of 60%. In line 17 in FIG. 5, the compounding ratio of the antibacterial component was level 2, and in line 18, the compounding ratio of the antibacterial component was level 1. As can be seen from FIG. 5, the volatilization amount of the antibacterial component volatilized by the bag is higher when the compounding ratio of the antibacterial component is higher.

Figure 6:
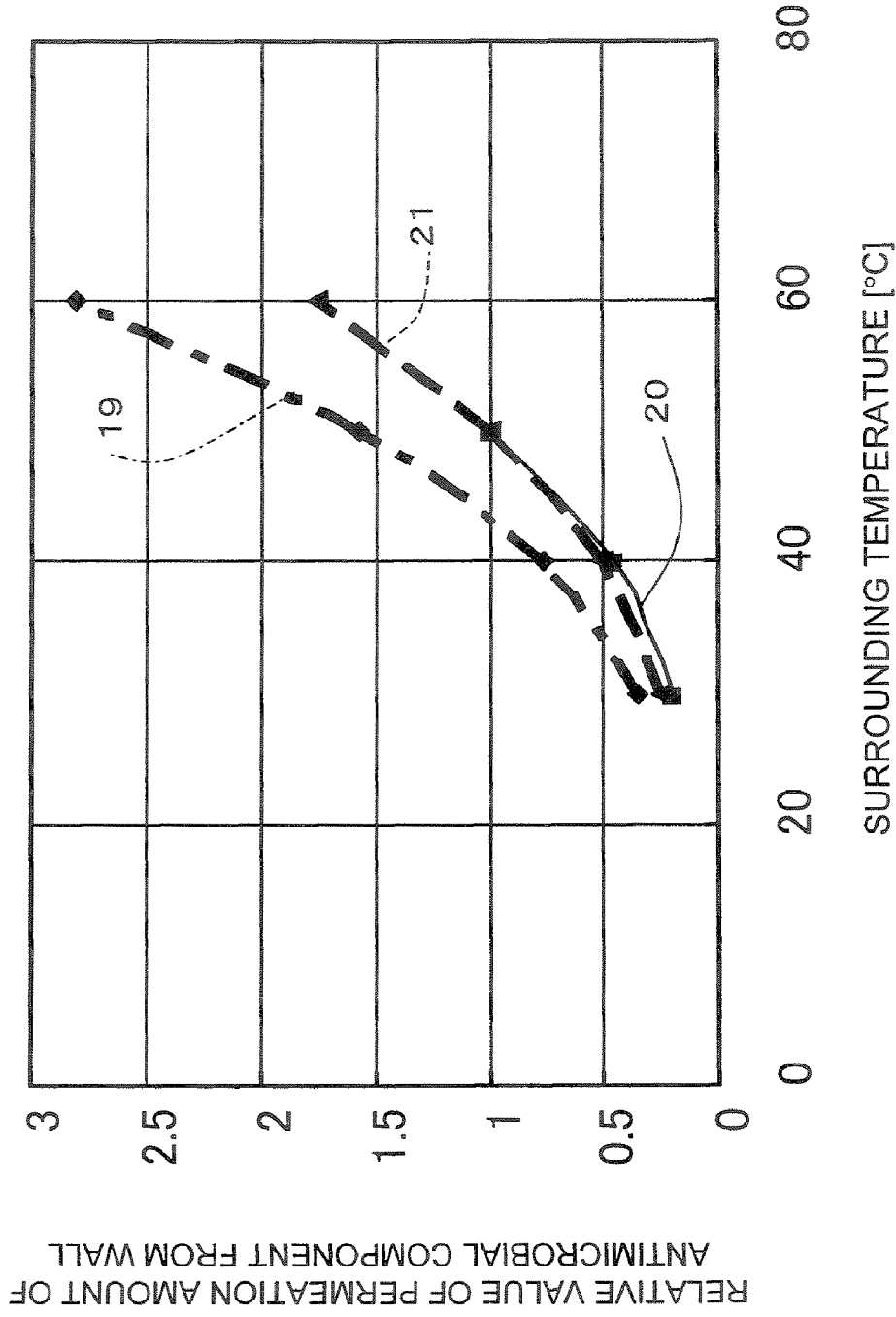
FIG. 6 is a graph showing the relationship between the shape ratio X/Y and the amount of the antibacterial component having permeated through the wall.

FIG. 6 is a graph showing the relationship between the shape ratio X/Y, that is, the ratio of the surface area X to the thickness Y of a wall of a case in which a bag is enclosed, the bag having a mixture containing an antibacterial component as a volatile substance enclosed therein, and the permeation amount of the antibacterial component having permeated the wall. In FIG. 6, the surrounding temperature (° C.) is shown on the abscissa, and the relative permeation amount of the antibacterial component from the wall is shown on the ordinate. In line 19 in FIG. 6, the shape ratio X/Y is 8000 and the compounding ratio of the antibacterial component is level 2 (the same ratio as the above-mentioned level 2). In line 20, the shape ratio X/Y is 8000 and the compounding ratio of the antibacterial component is level 1 (the same ratio as the above-mentioned level 1). In line 21, the shape ratio X/Y is 5000 and the compounding ratio of the antibacterial component is level 2 (the same ratio as the above-mentioned level 2). Given the same shape ratio X/Y of 8000, the permeation amount of the antibacterial component from the wall is greater at the higher compounding ratio of the antibacterial component, as shown in FIG. 6. Given the same compounding ratio of the antibacterial component, the permeation amount of the antibacterial component from the wall is greater at the higher shape ratio X/Y. The case where the shape ratio X/Y is 5000 and the compounding ratio of the antibacterial component is level 2 and the case where the shape ratio X/Y is 8000 and the compounding ratio of the antibacterial component is level 1 are approximately equal to each other in the permeation amount of the antibacterial component from the wall. It can be seen that given the same thickness of the wall for example, the surface area of the wall can be reduced by about 37.5% by doubling the compounding ratio of the antibacterial component.

Figure 7:
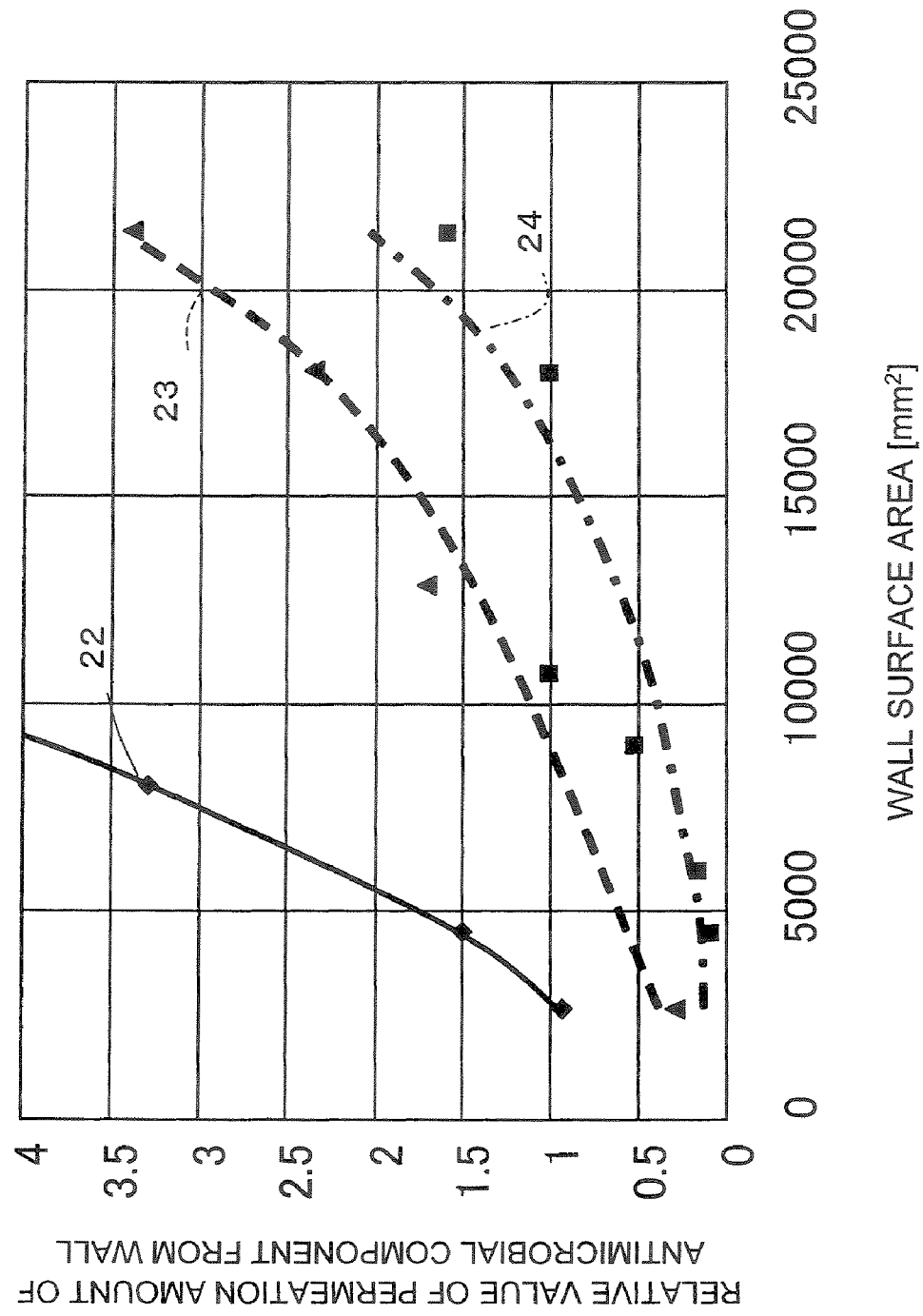
FIG. 7 is a graph showing the relationship between the amount of the antibacterial component having permeated through the bag and the amount of the antibacterial component having permeated through the wall.

FIG. 7 is a graph showing the relationship between the volatilization amount of an antibacterial component volatilized by a bag having a mixture containing an antibacterial component as a volatile substance enclosed therein, the bag being enclosed in a case, and the permeation amount of the antibacterial component having permeated the wall. In FIG. 7, the surface area X (mm$^2$) of the wall is shown on the abscissa, and the relative permeation amount of the antibacterial component from the wall is shown on the ordinate. In FIG. 7, the thickness Y (mm) of the wall is made constant. In line 22 in FIG. 7, the volatilization amount of the antibacterial component volatilized by the bag in an atmosphere at 30° C. is 100 mg/day. In line 23, the volatilization amount of the antibacterial component volatilized by the bag in an atmosphere at 30° C. is 50 mg/day. In line 24, the volatilization amount of the antibacterial component volatilized by the bag in an atmosphere at 30° C. is 25 mg/day. As a result of the inventors' examination, the amount of the antibacterial component necessary for an air conditioner for vehicles is in the range of 5 to 30 mg/day. For satisfying this range, the surface area of the wall should be 3000 to 6000 mm$^2$ when the volatilization amount of the antibacterial component volatilized by the bag is 100 mg/day. When the volatilization amount of the antibacterial component volatilized by the bag is 25 mg/day, the surface area of the wall should be 12000 to 30000 mm$^2$. In this way, the desired surface area of the wall varies depending on the volatilization amount of the antibacterial component volatilized by the bag.

According to the above-mentioned examination, production of a package having a shape adapted to the volumes and shapes of various air conditioners and capable of volatilizing an antibacterial agent at a predetermined rate requires adjustment of the package with 3 parameters, that is, the surface area X (mm$^2$) of the wall made of resin, the thickness Y (mm) of the wall made of resin, and the volatilization amount Z (mg/day) of an antibacterial component volatilized by the bag in an atmosphere at 30° C. The package of a volatile substance according to this embodiment overcomes the above-mentioned problem by defining the package in terms of the 3 parameters in the formula X×Z/Y so as to satisfy the formula such that the value expressed thereby is in the range of 200000 to 1500000.

Figure 8:
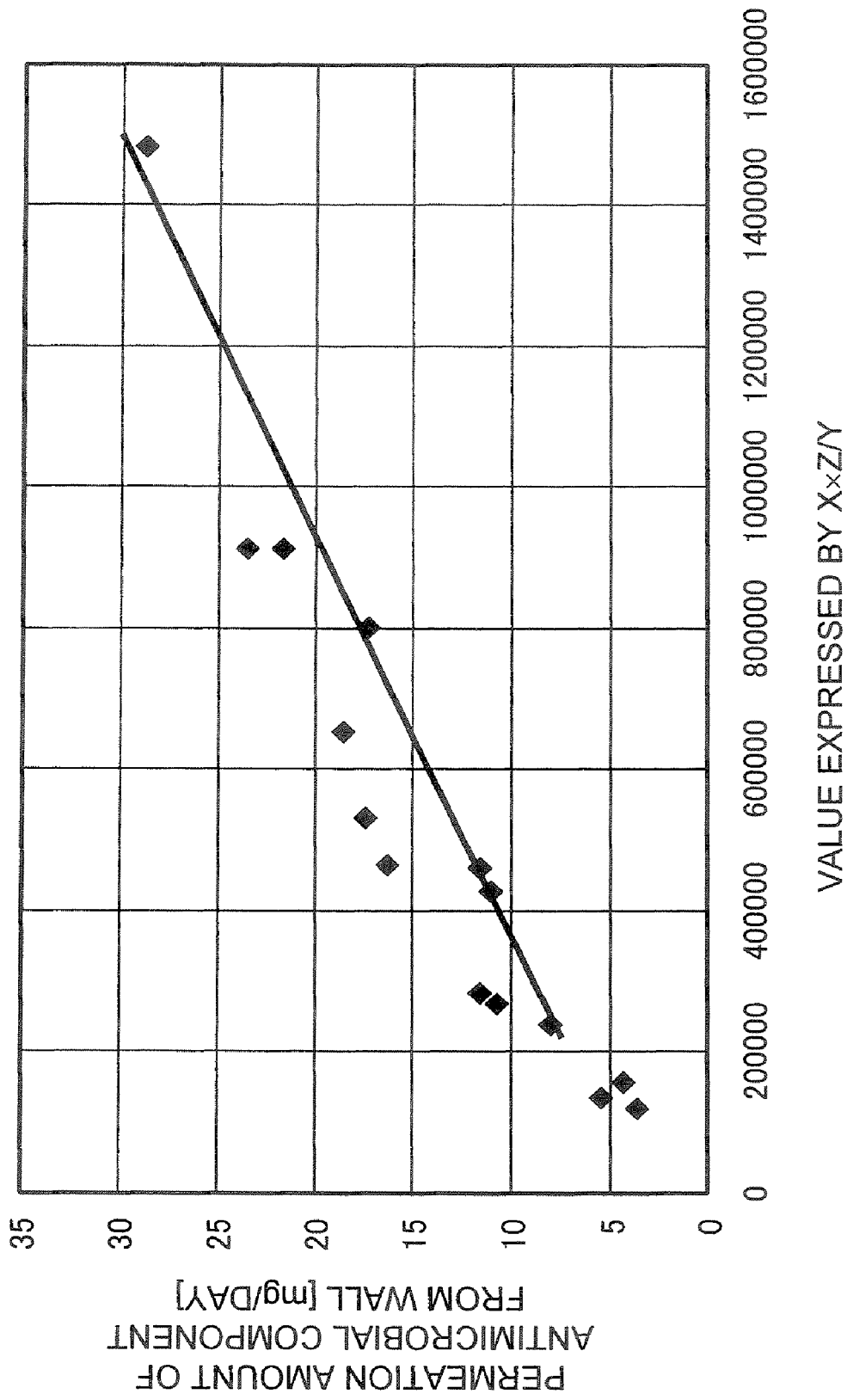
FIG. 8 is a graph showing the relationship between the value expressed by X×Z/Y and the amount of the antibacterial component having permeated through the wall.

FIG. 8 is a graph showing the relationship between the value expressed by X×Z/Y and the permeation amount of the antibacterial component having permeated the wall. In FIG. 8, the value expressed by X×Z/Y is shown on the abscissa, and the permeation amount (mg/day) of the antibacterial component from the wall is shown on the ordinate. It can be seen that when 5 to 30 mg/day of the antibacterial component having permeated the wall is necessary for an air conditioner for vehicles, the optimum value expressed by X×Z/Y is in the range of 200000 to 1500000.

As described above, the package 100 has a shape suitable for the volumes and shapes of various air conditioners and can simultaneously volatilize an antibacterial agent at a predetermined rate.

Figure 9:
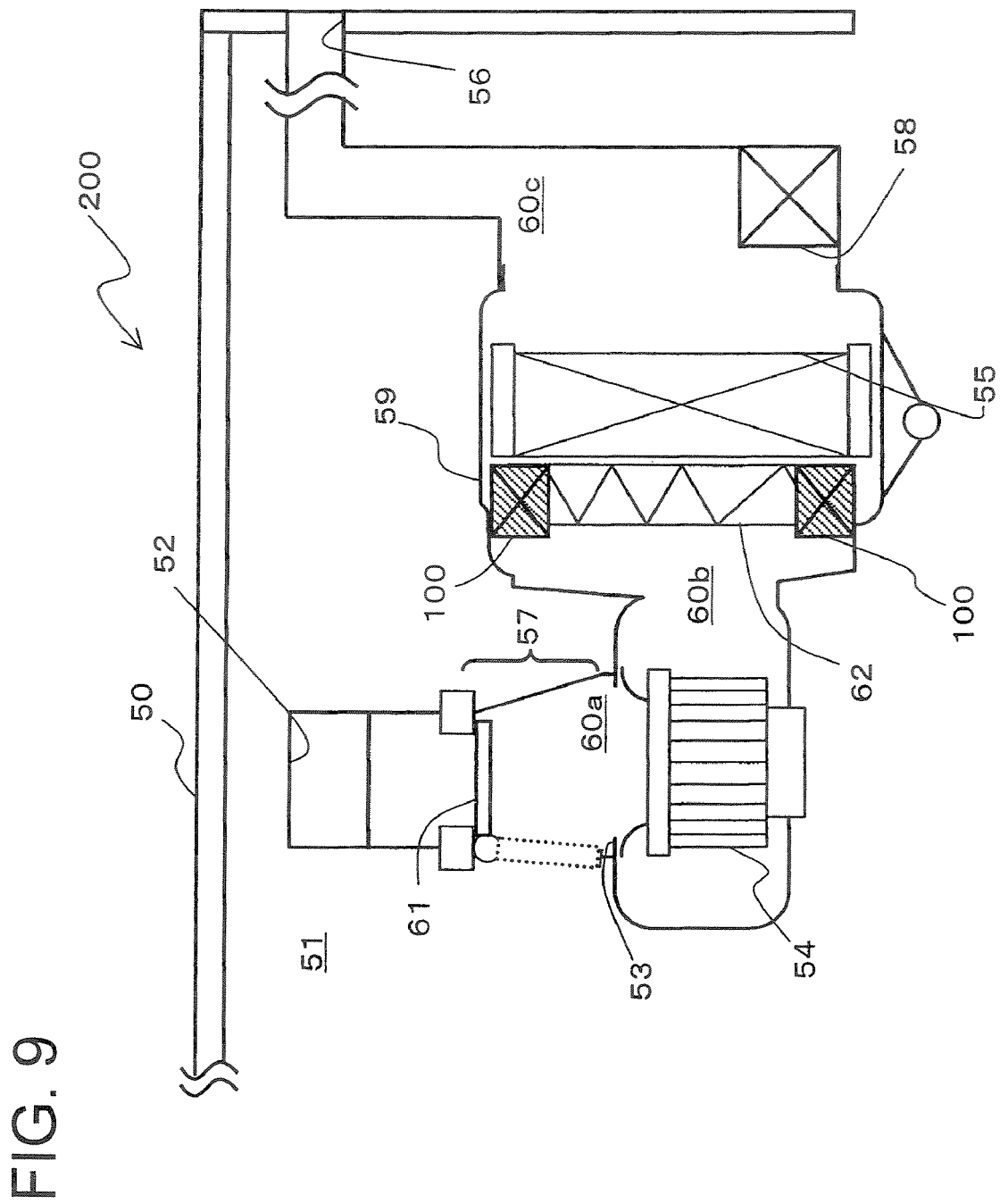
FIG. 9 is a schematic view showing one embodiment of the vehicle air-conditioning device (HVAC: Heating Ventilation and Air Conditioning) in accordance with the first embodiment.

Now, a method of using the package 100 for a volatile substance according to this embodiment is described by reference to an example wherein the package 100 is applied to HVAC. FIG. 9 is a schematic view showing one example of HVAC 200 according to this embodiment.

HVAC 200 is an apparatus which is housed in an internal space 51 of an instrument panel 50, incorporates air through a fresh-air inlet 52 or an in-car air suction opening 53, and exhales air from an in-car blowout opening 56 to an in-car space. HVAC 200 is composed of the fresh-air inlet 52, the in-car air suction opening 53, an inside/outside air switching box 57, a blower unit 54, ventilation ducts 60a, 60b, 60c forming an air stream by the operation of the blower unit 54, the package 100, a filter unit 62, an evaporator 55, a heater core 58, a housing 59 housing the filter unit 62, the evaporator 55 and the heater core 58, and the in-car blowout opening 56.

When components such as vehicle measuring meters and HVAC unit are arranged between unit a fire board (not shown) and a driver seat/passenger seat, the instrument panel 50 houses such components to divide the vehicle interior.

The fresh-air inlet 52, which is arranged on a wall surface of a fire board (not shown) that is a wall dividing a driver seat from an engine compartment, is an opening through which the inside/outside air switching box 57 communicates with the outside of the vehicle interior. The in-car air suction opening 53, which is arranged for example in an instrument panel 50 in a part in front of a passenger seat, is an opening through which the inside/outside air switching box 57 communicates with the inside of the vehicle interior. When HVAC 200 is used in a fresh air introduction mode (FRE mode), fresh air is incorporated by the operation of the blower unit 54 into HVAC 200. When HVAC 200 is used in an in-car air introduction mode (REC mode), in-car air is incorporated by the operation of the blower unit 54 into HVAC 200. The inside/outside air switching box 57 switches between REC mode and FRE mode by an intake door 61.

The blower unit 54 is arranged in the ventilation ducts 60a, 60b and 60c in the housing 59, to form an air stream in the ventilation ducts 60a, 60b and 60c. In FIG. 9, the blower unit 54 is expressed as a sirocco fan, which is centrifugal, but may be a turbofan or may also be a flow-through blower.

The package 100 is the package of a volatile substance according to the present invention. The package 100 is may arranged in any of the ventilation ducts 60a, 60b and 60c. For example, the package 100 may be arranged upstream of the blower unit 54 or may be arranged upside or downside of the filter unit 62, in the ventilation duct 60b between the blower unit 54 and evaporator 55, as shown in FIG. 9. The package 100 may function to allow the volatile substance to be permeated through The evaporator 55 constitutes an air-conditioning refrigeration cycle. The refrigeration cycle is provided with at least a compressor (not shown) for compressing a cooling medium in a vaporized state and discharging it, a condenser (not shown) for condensing the cooling medium discharged from the compressor, an expansion valve (not shown) for converting the cooling medium condensed with the condenser into a gas/liquid mixture by a squeezing action, and the evaporator 55 for cooling and dehumidifying air by the evaporation heat of the cooling medium converted into a gas/liquid mixture by the expansion valve. The heater core 58 and an air mix door (not shown) are arranged downstream of the evaporator 55, and further downstream thereof, a blowout opening such as a bent blowout opening (not shown), a side bent blowout opening (not shown), a defroster gear blowout opening (not shown) or a foot blowout opening (not shown) is arranged as the in-car blowout opening 56.

Now, diffusion of the volatile substance volatilized from the package in HVAC 200 is described by reference to an example of the package 100 arranged in a ventilation duct 60b between a blower unit 54 and an evaporator 55, as shown in FIG. 9. For example, when HVAC 200 is not operated such as in parking, the volatile substance is volatilized from the package 100 due to arise in temperature in a car. The volatilized volatile substance is diffused toward the evaporator 55 and blower unit 54 by natural convection. The volatile substance such as an antibacterial agent can spread to the evaporator 55 and blower unit 54 in HVAC 200, where dew drops are particularly generated to permit easy proliferation of bacteria. When HVAC 200 is operated, an air stream directed from the fresh-air inlet 52 or in-car air suction opening 53 to the in-car blowout opening 56 is formed through ventilation ducts 60a, 60b, 60c. Accordingly, the volatile substance volatilized from the package 100 spreads throughout components downstream of the package 100, such as evaporator 55 and heater core 58. The volatile substance is preferably an isothiocyanate compound, particularly preferably AIT. AIT is a compound known as a major component of Japanese horseradish, can be used as an antibacterial agent and is a highly safe substance which can also be utilized in foods. Accordingly, the volatile substance is safe even when discharged through the in-car blowout opening 56 toward the passenger.

By constituting such HVAC 200, HVAC can reduce an inside offensive odor.

Second Embodiment

Figure 10:
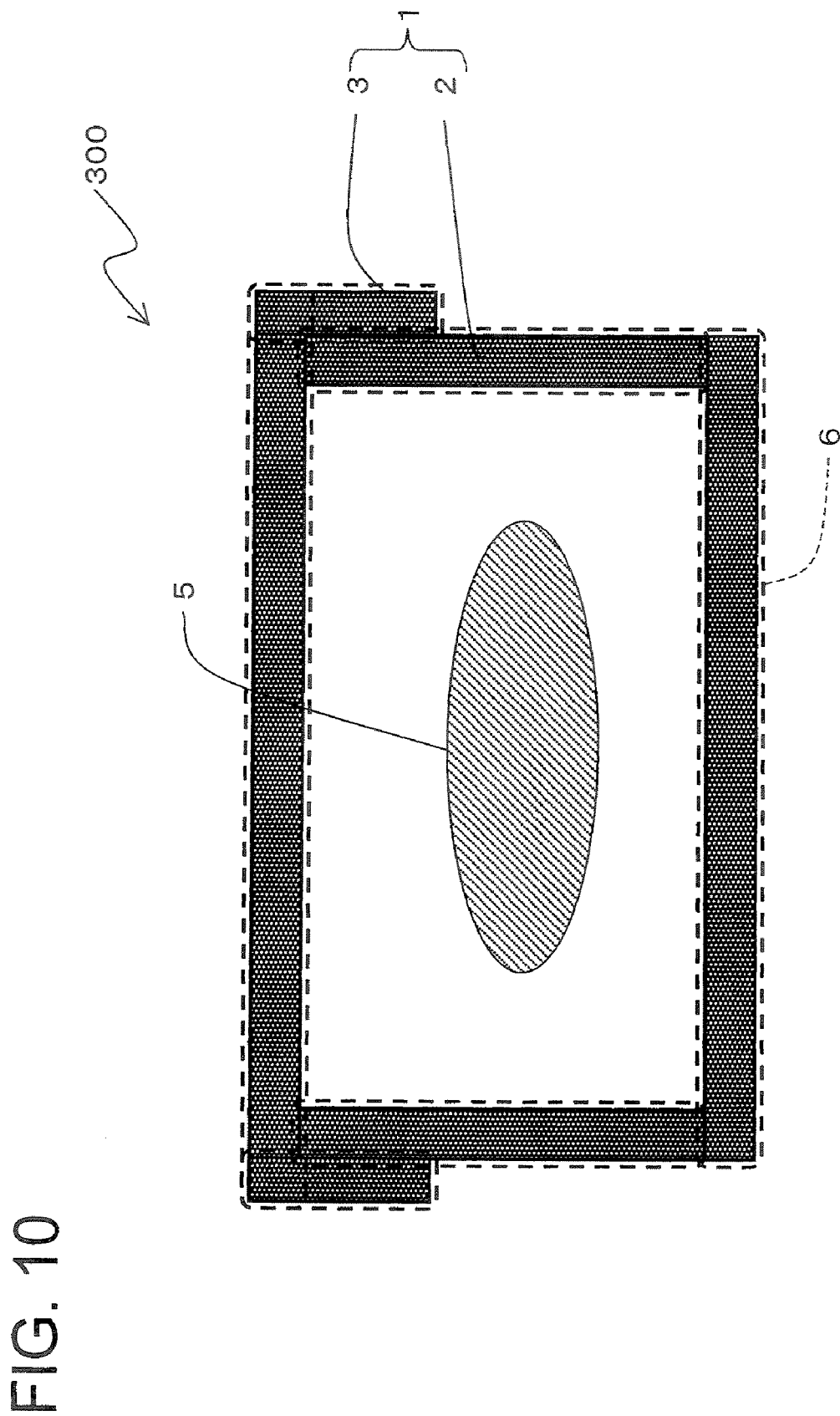
FIG. 10 is a schematic view of a section A-A' of the package of a volatile substance in accordance with the second embodiment.

In the package 300 for a volatile substance in accordance with this embodiment, a source for generating a volatile substance is formed into a mixture having the volatile substance supported in an arbitrary compounding ratio on at least one or more kind of support, and the mixture is enclosed directly in a case. The package 300 for a volatile substance in accordance with this embodiment is shown in FIG. 10. The package 300 is different only in the absence of a bag from the package 100 in accordance with the first embodiment. Accordingly, the package 300 is the same as the package 100 in respect of the component of the volatile substance, the component of the mixture 5, the material, shape and size of the case 1, the volatilization mechanism of the volatile substance, the permeation characteristics of the volatile substance in the case 1, and application to HVAC 200.

EXAMPLES

Relationship Between the Amount of a Volatile Substance Capable of Permeating the Package and X×Z/Y In Examples 1 to 4, it was verified that when it is satisfied by the package of a volatile substance according to the present invention that a value expressed by the formula X×Z/Y is 200000 to 1500000 wherein X represents the surface area ($mm^2$) of the resin wall of the package; Y represents the thickness (mm) of the wall made of resin; and Z represents the vaporization amount (mg/day) of the volatile substance volatilized by the bag per day in an atmosphere at 30° C., the amount of the volatile substance which can be volatilized from the package is in the range of 5 to 30 mg/day that is an amount effective in suppressing microbial growth in a vehicle air conditioner.

Example 1

In Example 1, the amount of a volatile substance (AIT) capable of permeating the package was measured wherein the surface area X (mm$^2$) of the wall was 8500 mm$^2$, the thickness Y (mm) of the wall was 0.8 mm, and the volatilization amount Z (mg/day) of the volatile substance volatilized by the bag in an atmosphere at 30° C. was 50 mg/day. The amount of AIT having permeated the bag and package was determined by measuring a reduction in weight with time. The bag used in Example 1 was a bag having a plurality of sheets laminated therein. Sheets with the following thickness were laminated in the following order from the outside: a sheet consisting of a nonwoven fabric, 14 g/m$^2$; a sheet consisting of polyethylene, 15 µm; a sheet consisting of biaxially stretched polypropylene, 40 µm; and a sheet consisting of polyethylene, 30 µm. The compounding ratio of the antibacterial component was level 1 shown in FIG. 5.

The value expressed by X×Z/Y in Example 1 was 531250, which is within the range required for the package of a volatile substance according to the present invention. The measured amount of AIT having permeated the package in Example 1 was 18 mg/day and could be confirmed to be an amount effective in suppressing microbial growth in an air conditioner for vehicles.

Example 2

In Example 2, the amount of a volatile substance (AIT) capable of permeating the package was measured wherein the surface area X (mm$^2$) of the wall was 3900 mm$^2$, the thickness Y (mm) of the wall was 0.9 mm, and the volatilization amount Z (mg/day) of the volatile substance volatilized by the bag in an atmosphere at 30° C. was 94 mg/day. In the measurement, the same instrument as in Example 1 was used. In Example 2, the same bag as in Example 1 was used. The compounding ratio of the antibacterial component was level 2 shown in FIG. 5.

The value expressed by X×Z/Y in Example 2 was 407333, which is within the range required for the package of a volatile substance according to the present invention. The determined amount of AIT having permeated the package in Example 2 was 12 mg/day and could be confirmed to be an amount effective in suppressing microbial growth in an air conditioner for vehicles.

Example 3

In Example 3, the amount of AIT capable of permeating the package was measured wherein the surface area X (mm$^2$) of the wall was 8500 mm$^2$, the thickness Y (mm) of the wall was 0.8 mm, and the volatilization amount Z (mg/day) of the volatile substance volatilized by the bag in an atmosphere at 30° C. was 140 mg/day. In the measurement, the same instrument as in Example 1 was used. The bag used in Example 3 was a bag having a plurality of sheets laminated therein. Sheets with the following thickness were laminated in the following order from the outside: a sheet consisting of a nonwoven fabric, 14 g/m$^2$; a sheet consisting of polyethylene, 15 µm; a sheet consisting of biaxially stretched polypropylene, 20 µm; and a sheet consisting of polyethylene, 30 µm. The compounding ratio of the antibacterial component was level 1 shown in FIG. 5.

The value expressed by X×Z/Y in Example 3 was 1487500, which is within the range required for the package of a volatile substance according to the present invention. The determined amount of AIT having permeated the package in Example 3 was 28 mg/day and could be confirmed to be an amount effective in suppressing microbial growth in an air conditioner for vehicles.

Example 4

In Example 4, the amount of a volatile substance (AIT) capable of permeating the package was measured wherein the bag is absent, the surface area X (mm$^2$) of the wall was 8500 mm the thickness Y (mm) of the wall was 0.9 mm, and the volatilization amount Z (mg/day) of the volatile substance volatilized by the mixture in an atmosphere at 30° C. was 150 mg/day. The amount of AIT having permeated the package was determined by measuring a reduction in weight with time. To prepare the mixture in Example 4, 46.5 parts by mass of rosin ester and 18.6 parts by mass of paraffin wax were heated and melted in a tank capable of being hermetically closed. Thereafter, 11.6 parts by mass of AIT were added, and further, 23.3 parts by mass of porous cellulose particles were added, followed by cooling and solidification. The mixture was thereby obtained.

The value expressed by X×Z/Y in Example 4 was 1416667, which is within the range required for the package of a volatile substance according to the present invention. The determined amount of AIT having permeated the package in Example 4 was 26 mg/day and could be confirmed to be an amount effective in suppressing microbial growth in an air conditioner for vehicles.

When Example 1 is compared with Example 4, the amount of AIT permeating through the package could be increased by increasing the value expressed by X×Z/Y.

Evaluation of Antibacterial Effect

The HVAC provided with the package of a volatile substance according to the present invention was used to evaluate the antibacterial effect. In this evaluation, HVAC provided therein with the package of a volatile substance according to the present invention was evaluated as Example 5, and HVAC not provided with the package of a volatile substance was evaluated as Comparative Example 1. The same package as in Example 1 was used. The results are shown in FIG. 11. The evaluation months are shown on the abscissa, and the number of microorganisms per unit volume of drain water (number/ml) discharged upon operation of HVAC is shown on the ordinate. In FIG. 11, line 25 shows Example 5 and line 26 shows Comparative Example 1. The result indicated that in Example 5, the number of microorganisms is rapidly reduced from the beginning of the rainy season (June) when the evaluation was initiated and a tendency for increase in the number of microorganisms is not observed even in summer (July to August) because of the effect of the antibacterial agent volatilized by the volatile-substance package according to the present invention. In September when the air comes to be dry, the number of microorganisms is further decreased. In Comparative Example 1, on the other hand, the number of microorganisms is rapidly increased in the rainy season, and the number of microorganisms is kept high in summer (July to August) as well. Example 5 and Comparative Example 1 give the result in which the number of microorganisms in Example 5 is two-digit lower than in Comparative Example 1. Accordingly, it can be said that the HVAC provided with the package of a volatile substance according to the present invention can reduce microorganisms and is consequently effective in suppressing an offensive odor from the inside of HVAC.

The invention claimed is:

1. A package of a volatile substance, comprising:
a source generating the volatile substance, and
a case which has the source generating the volatile substance enclosed therein and which has a wall at least part of which is made of a gas-permeable resin,
wherein the source generating the volatile substance is a gas-permeable bag having the volatile substance enclosed therein; the thickness of the bag is 40 to 180 μm; the volatile substance is formed into a mixture having the volatile substance supported in an arbitrary compounding ratio on at least one or more kind of support, and the mixture is enclosed in the bag; the case is characterized in that a value expressed by the formula $X \times Z/Y$ is 200,000-1,500,000 where X represents the surface area ($mm^2$) of the wall made of the gas-permeable resin; Y represents thickness (mm) of the wall made of the gas-permeable resin; and Z represents the volatilization amount (mg/day) of the volatile substance volatilized by the source generating the volatile substance per day in an atmosphere at 30° C.

2. The package of a volatile substance according to claim 1, wherein the case allows the volatile substance to permeate therethrough at a rate of 5 to 30 mg/day in an atmosphere of 30° C.

3. The package of a volatile substance according to claim 1, wherein the bag is a bag provided partially or wholly with a permeation-regulating layer for regulating the permeation amount of the volatile substance.

4. The package of a volatile substance according to claim 3, wherein the bag comprises a sheet consisting of a non-woven fabric, a sheet consisting of polyethylene, a sheet consisting of a biaxially stretched polypropylene and a sheet consisting of polyethylene laminated in this order from the outside.

5. The package of a volatile substance according to claim 1, wherein the bag allows the volatile substance to permeate therethrough at a rate of 10 to 1000 mg/day in an atmosphere of 30° C.

6. The package of a volatile substance according to claim 3, wherein the bag allows the volatile substance to permeate therethrough at a rate of 10 to 1000 mg/day in an atmosphere of 30° C.

7. The package of a volatile substance according to claim 4, wherein the bag allows the volatile substance to permeate therethrough at a rate of 10 to 1000 mg/day in an atmosphere of 30° C.

8. The package of a volatile substance according to claim 1, wherein the volatile substance is an isothiocyanate compound.

9. The package of a volatile substance according to claim 1, wherein the gas-permeable resin forming the case is polypropylene.

10. An air conditioning device for vehicles, which comprises the package of a volatile substance according to claim 1, arranged in a ventilation duct.

11. The package of a volatile substance according to claim 1, wherein the source generating the volatile substance is supported on at least one support selected from the group consisting of a rosin, a rosin ester, a paraffin wax, a pulp, a paper, a cellulose particle, a zeolite, an alumina, a silica gel, and a calcium silicate.

12. A package of a volatile substance, comprising:
a source generating the volatile substance, and
a case which has the source generating the volatile substance enclosed therein and which has a wall at least a part of which is made of a gas-permeable resin,
wherein the source generating the volatile substance is a mixture having the volatile substance supported in a compounding ratio of 10 to 90% on at least one or more kind of support; the case is characterized in that a value expressed by the formula $X \times Z/Y$ is 200,000-1,500,000 where X represents the surface area ($mm^2$) of the wall made of the gas-permeable resin; Y represents the thickness (mm) of the wall made of the gas-permeable resin; and Z represents the volatilization amount (mg/day) of the volatile substance volatilized by the source generating the volatile substance per day in an atmosphere of 30° C.

13. The package of a volatile substance according to claim 12, wherein the case allows the volatile substance to permeate therethrough at a rate of 5 to 30 mg/day in an atmosphere of 30° C.

14. The package of a volatile substance according to claim 12, wherein the volatile substance is an isothiocyanate compound.

15. The package of a volatile substance according to claim 12, wherein the gas-permeable resin forming the case is polypropylene.

16. An air conditioning device for vehicles, which comprises the package of a volatile substance according to claim 12, arranged in a ventilation duct.

17. The package of a volatile substance according to claim 12, wherein the source generating the volatile substance is supported on at least one support selected from the group consisting of a rosin, a rosin ester, a paraffin wax, a pulp, a paper, a cellulose particle, a zeolite, an alumina, a silica gel, and a calcium silicate.

* * * * *